US007465545B2

(12) United States Patent
Kim et al.

(10) Patent No.: US 7,465,545 B2
(45) Date of Patent: Dec. 16, 2008

(54) MICROFLUIDIC CHIP AND MANIPULATING APPARATUS HAVING THE SAME

(75) Inventors: Su-hyeon Kim, Seoul (KR); Jun-hong Min, Yongin-si (KR); Kak Namkoong, Seoul (KR)

(73) Assignee: Samsung Electronics Co., Ltd. (KR)

( * ) Notice: Subject to any disclaimer, the term of this patent is extended or adjusted under 35 U.S.C. 154(b) by 303 days.

(21) Appl. No.: 11/341,033

(22) Filed: Jan. 27, 2006

(65) Prior Publication Data

US 2006/0185584 A1 Aug. 24, 2006

(30) Foreign Application Priority Data

Jan. 29, 2005 (KR) ...................... 10-2005-0008347

(51) Int. Cl.
*C12Q 1/68* (2006.01)
*C12P 19/34* (2006.01)

(52) U.S. Cl. .......................... 435/6; 435/91.1; 435/91.2

(58) Field of Classification Search ....................... None
See application file for complete search history.

(56) References Cited

U.S. PATENT DOCUMENTS 4,963,498 A 10/1990 Hillman et al.
6,368,871 B1 * 4/2002 Christel et al. .............. 436/180
6,408,878 B2 6/2002 Unger et al.
2003/0146155 A1 * 8/2003 Tooke et al. ................ 210/651
2003/0190608 A1 10/2003 Blackbum

OTHER PUBLICATIONS

2-D Modeling and Simulation of Fluidic Microsystems for Biological Fluids Analysis; G. Minas*,J.C. Ribeiro, R.F. Wolffenbuttel**, J.H. Correia*; pp. 239-242; *University of Minho, dept. of Industrial Electronics, Campus deAzurem, 4800-058 Guimaraes, Portugal; **Delft University of Technology, Fac. ITS Dept. Microelectronics, Mekelweg 4, 2628 CD Delft, The Netherlands.

* cited by examiner

*Primary Examiner*—Young J Kim
(74) *Attorney, Agent, or Firm*—Cantor Colburn LLP

(57) ABSTRACT

Provided are a microfluidic chip and a microfluidic manipulating apparatus including the same. The microfluidic chip includes at least one microfluidic manipulating unit formed in a substrate. The microfluidic manipulating unit includes: a plurality of microchannels formed in the substrate; an inlet formed at a first end of the microchannel and exposed through the substrate; a trap formed at the microchannel; a chamber connected to a second end of the microchannel; and an outlet connected to the chamber and exposed through the substrate.

16 Claims, 8 Drawing Sheets

MICROFLUIDIC CHIP AND MANIPULATING APPARATUS HAVING THE SAME

CROSS-REFERENCE TO RELATED PATENT APPLICATIONS

This application claims the benefit of Korean Patent Applications Nos. 10-2005-0008347 and 10-2005-0121905, filed on Jan. 29, 2005, and on Dec. 12, 2005, respectively in the Korean Intellectual Property Office, the disclosures of which are incorporated herein in their entirety by reference.

BACKGROUND OF THE INVENTION

1. Field of the Invention

The present invention relates to a microfluidic chip containing a microfluidic trap formed of a microchannel and a manipulating apparatus.

2. Description of the Related Art

Microfluidics is a field in which a microchannel is formed by photolithography, hot embossing, molding, or the like in a microfluidic chip such that the movement or mixing of microfluids can be manipulated. When a single microfluidic chip includes a plurality of microchannels, the amount of the sample consumed decreases and the analysis time shortens.

Pumps and valves are needed to manipulate microfluid contained in a microchannel. In particular, a plurality of pumps and valves are required to manipulate a plurality of microfluids.

Microfluidic chips have become more miniaturized as micro processing techniques have developed. However, in order to achieve the miniaturization of a lab-on-a-chip, the sizes of mechanical pumps and valves must be decreased. Accordingly, there have been many attempts to find substitutes for the mechanical pumps and valves in microfluidics.

For example, U.S. Pat. No. 6,408,878 discloses an elastic valve in a microchannel and a method of opening/closing the elastic valve. In this case, however, a mechanical pump is required.

In addition, U.S. Pat. No. 4,963,498 discloses a method of transferring fluid using centrifugal force. In this case, however, the centrifugal force must be adjusted, and portions having different surface tensions are needed to be formed at an inner surface of a microchannel.

SUMMARY OF THE INVENTION

The present invention provides a microfluidic chip containing a microfluidic trap formed of a micro channel.

The present invention also provides a manipulating apparatus capable of changing a direction of a centrifugal force applied to the microfluidic chip.

According to an aspect of the present invention, there is provided a microfluidic chip including at least one microfluidic manipulating unit formed in a substrate, the microfluidic manipulating unit including: a plurality of microchannels formed in the substrate; an inlet formed at a first end of the microchannel and exposed through the substrate; a trap formed at the microchannel; a chamber connected to a second end of the microchannel; and an outlet connected to the chamber and exposed through the substrate.

The trap may be U-shaped.

The trap may make an acute angle with respect to a first direction in which a liquid injected through the inlet flows.

The trap may include a first trap, wherein the first trap traps liquid when a centrifugal force is applied in the first direction, or a second direction perpendicular to the first direction making an acute angle with respect to the first trap.

The trap may further include a second trap formed between the first trap and the chamber, and the second trap traps the liquid when a centrifugal force is applied in a third direction opposite to the second direction and a fourth direction opposite to the first direction.

The second trap is formed in an opposite direction to a direction in which the first trap is formed.

The outlet may be formed in the second direction.

According to another aspect of the present invention, there is provided an apparatus for manipulating microfluid including: a rotating plate; a microfluidic chip fixedly disposed on the rotating plate; a first driving unit which rotates the rotating plate; and a second driving unit which rotates the microfluidic chip on the rotating plate, wherein the microfluidic chip includes at least one microfluidic manipulating unit including: a plurality of microchannels formed in the substrate; an inlet formed at a first end of the microchannel and exposed through the substrate; a trap formed at the microchannel; a chamber connected to a second end of the microchannel; and an outlet connected to the chamber and exposed through the substrate.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
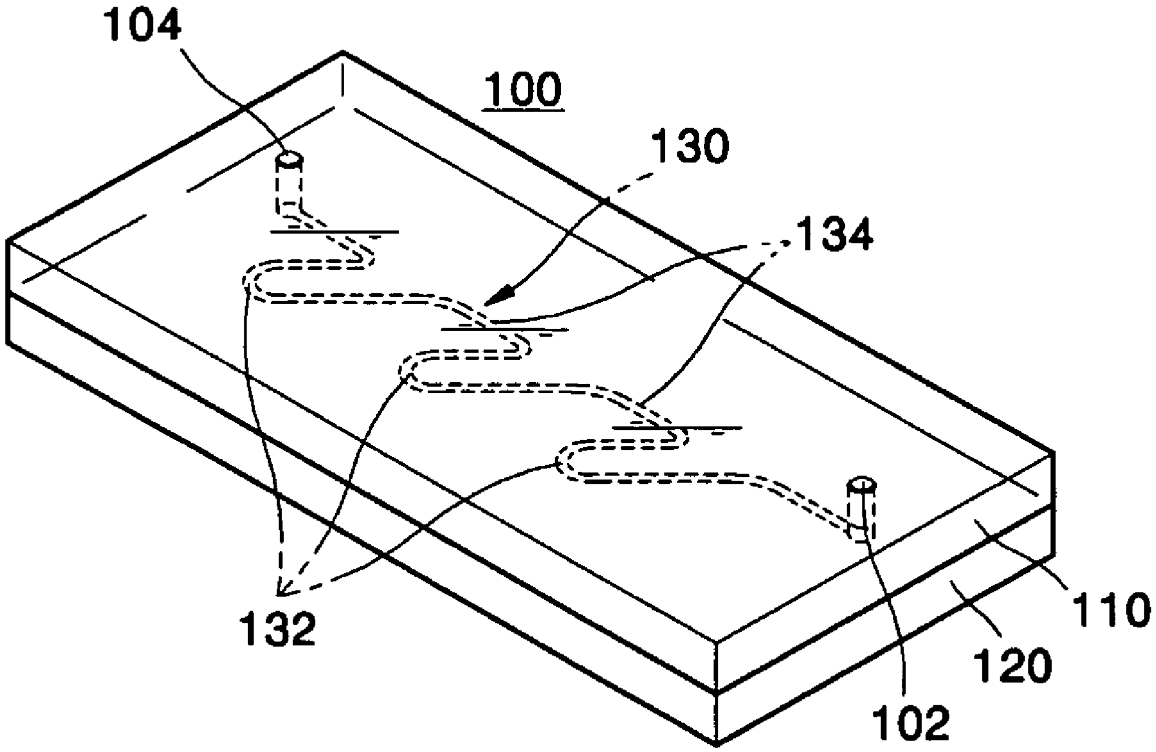
FIG. 1 is a perspective view of a microfluidic chip according to a first embodiment of the present invention.

Microfluidic chips according to embodiments of the present invention and an manipulating apparatus including the same will now be described in detail with reference to the accompanying drawings. In the drawings, the thicknesses of layers and regions are exaggerated for clarity.

FIG. 1 is a perspective view of a microfluidic chip 100 according to a first embodiment of the present invention.

Referring to FIG. 1, the microfluidic chip 100 includes an upper substrate 110 having a sample inlet 102 and a sample outlet 104, and a lower substrate 120. A microchannel 130 is formed between the upper substrate 110 and the lower substrate 120. The microchannel 130 can be formed in one of the upper substrate 110 and the lower substrate 120 and is capped by the other substrate. Alternatively, the microchannel 130 can be formed by forming an exposed groove in each of the upper substrate 110 and the lower substrate 120 and combining the grooves. The sample inlet 102, the sample outlet 104, and the microchannel 130 may be formed using photolithography, hot-embossing, or plastic molding.

The microchannel 130 has first traps 132 inclined with respect to a direction from the inlet 102 to the sample outlet 104. The first traps 132 are U-shaped. Second traps 134 formed in an opposite direction to a direction in which the first traps 132 are formed. The first traps 132 and the second traps 134 are alternatively formed.

The upper substrate 110 is coupled with the lower substrate 120 using anodic bonding, thermal bonding, or an adhesive such that the resulting structure can store liquid. The microfluidic chip 100 may be made of silicon, plastic, glass, or the like.

Figure 2A:
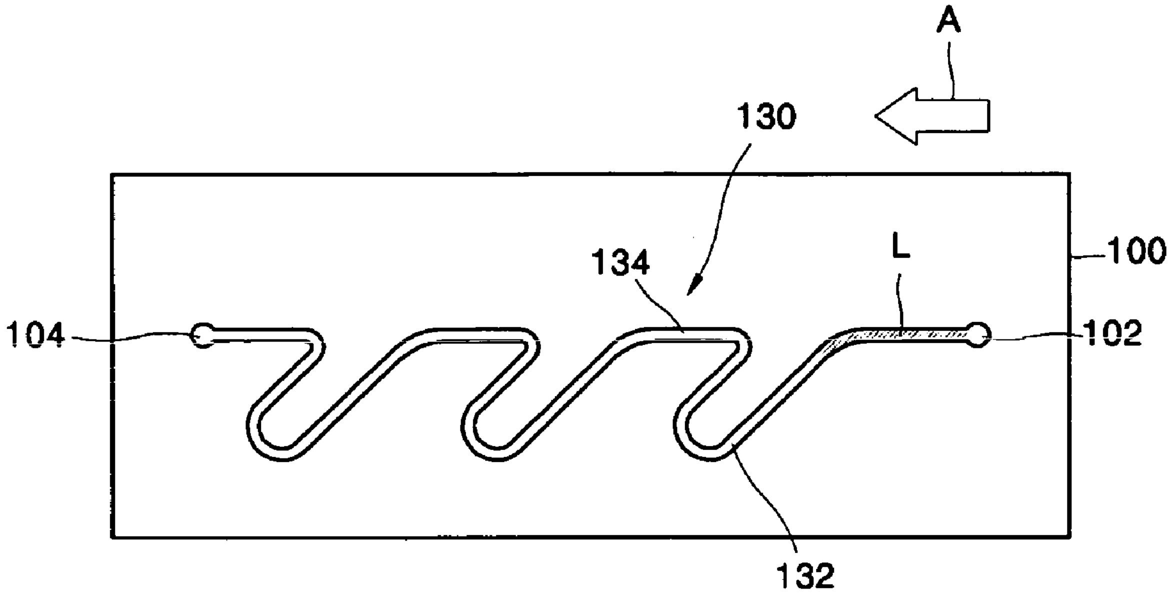
FIGS. 2A through 2C are plan views illustrating the operation of the microfluidic chip illustrated in FIG. 1.
Figure 2B:
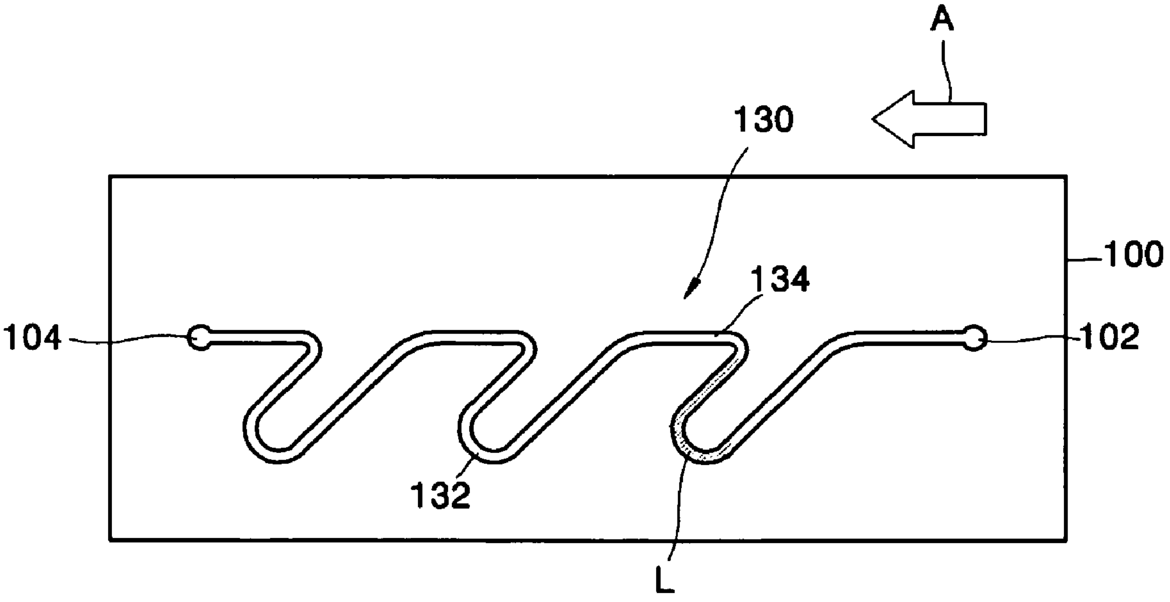
Figure 2C:
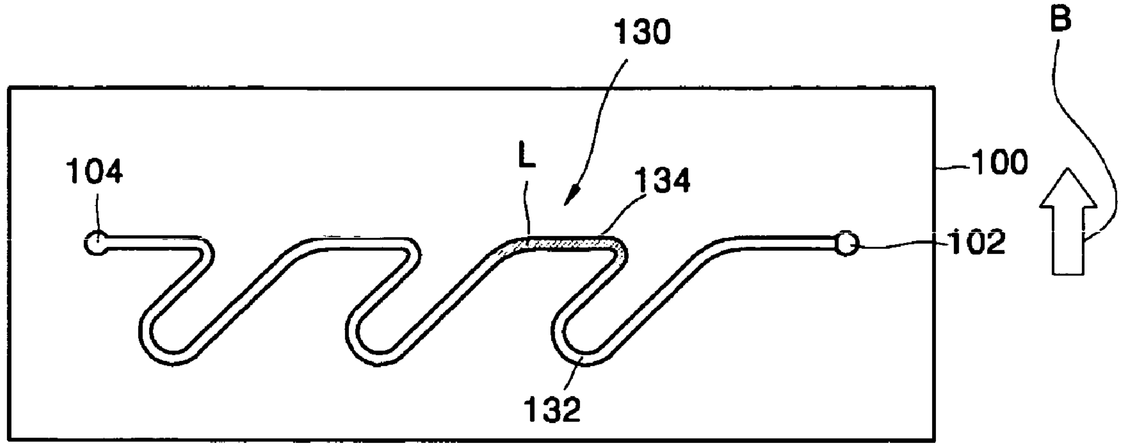

FIGS. 2A through 2C are plan views illustrating the operation of the microfluidic chip 100 of FIG. 1.

Referring to FIG. 2A, a liquid L is injected through the inlet 102 of the microfluidic chip 100. When a predetermined force, for example, a centrifugal force, is applied to the liquid L in an arrow A direction, the liquid L flows to the first trap 132 in the arrow A direction. The first trap 132 may be formed at an acute angle with respect to the arrow A direction, for example, 45°.

Referring to FIG. 2B, even when the centrifugal force is continually applied in the arrow A direction, the liquid L does not flow further forward the outlet 104. Instead, the liquid L is trapped in the trap 132 of the microchannel 130.

Referring to FIG. 2C, when a centrifugal force is applied in an arrow B direction, the liquid L flows upward and is trapped in the second trap 134. That is, the liquid L flows a predetermined distance to the left. Although the centrifugal force is continually applied in the arrow B direction, the liquid L does not flow further.

The liquid L can flow from the inlet 102 to the outlet 104 by repeating the operations illustrated in FIGS. 2B and 2C.

Figure 3:
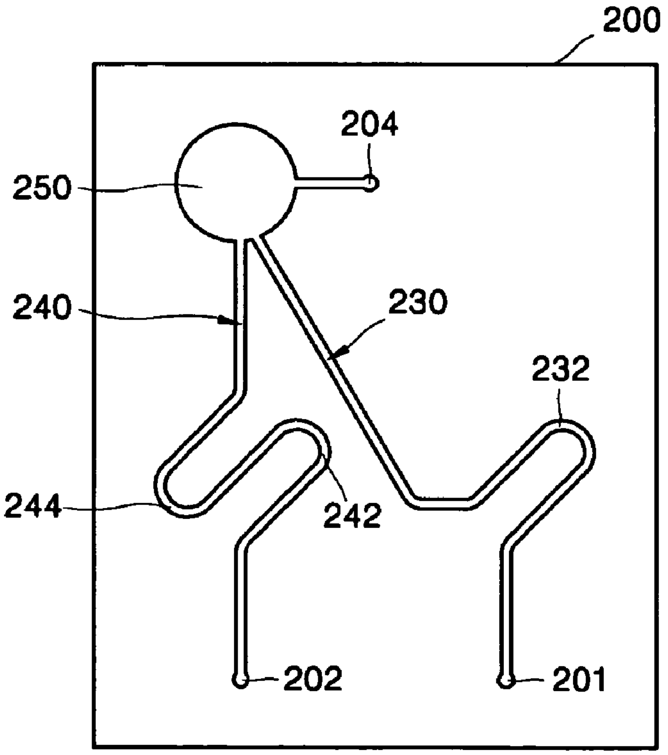
FIG. 3 is a plan view of a microfluidic chip according to a second embodiment of the present invention.

FIG. 3 is a plan view of a microfluidic chip 200 according to a second embodiment of the present invention.

Referring to FIG. 3, the microfluidic chip 200 includes first and second inlets 201 and 202, a chamber 250, an outlet 204, and first and second microchannels 230 and 240 connecting the inlets 201 and 202 to the chamber 250. The first microchannel 230 has a first trap 232, and the second microchannel 240 has first and second traps 242 and 244. Ends of the first and second microchannels 230 and 240 are connected to the first and second inlets 201 and 202, respectively. Other ends of the first and second microchannels 230 and 240 are connected to a side of the chamber 250.

The outlet 204 is connected to a side of the chamber 250 almost perpendicular to the side of the chamber 250 to which the microchannels 230 and 240 are connected. The traps 232, 242, and 244 are U-shaped, and formed at an acute angle with respect to a liquid flowing direction in which a centrifugal force is applied, for example, 45°.

FIGS. 4A through 4E are plan views illustrating the operation of the microfluidic chip illustrated in FIG. 3.

Figure 4A:
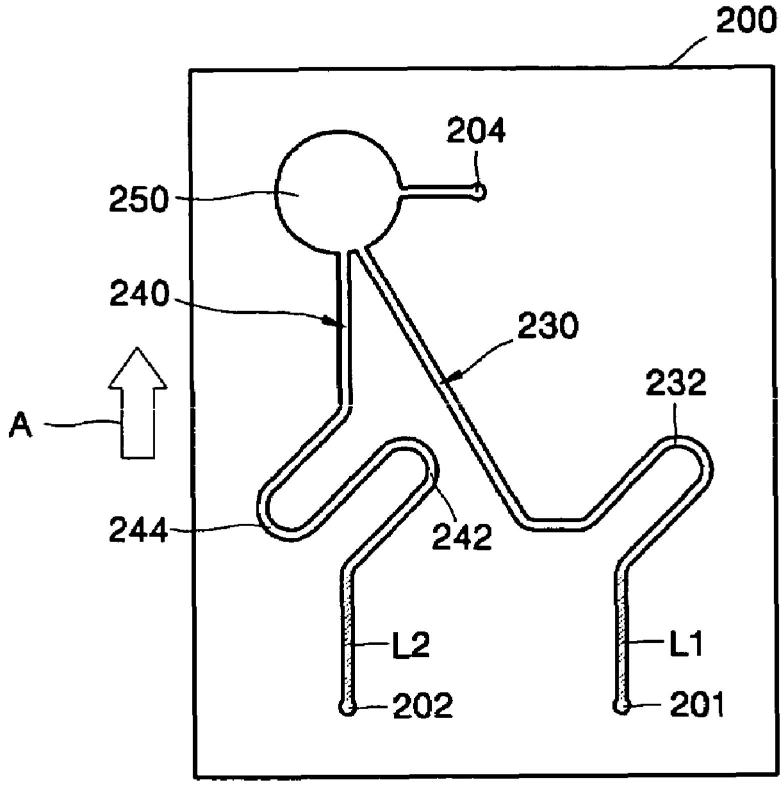
FIGS. 4A through 4E are plan views illustrating the operation of the microfluidic chip illustrated in FIG. 3.

Referring to FIG. 4A, a first liquid L1 and a second liquid L2 are injected through the first inlet 201 and the second inlet 202, respectively. Then, a predetermined force such as a centrifugal force is applied to the microfluidic chip 200 in a first direction indicated by an arrow, so that the first and second liquids L1 and L2 flow in the first direction.

Figure 4B:
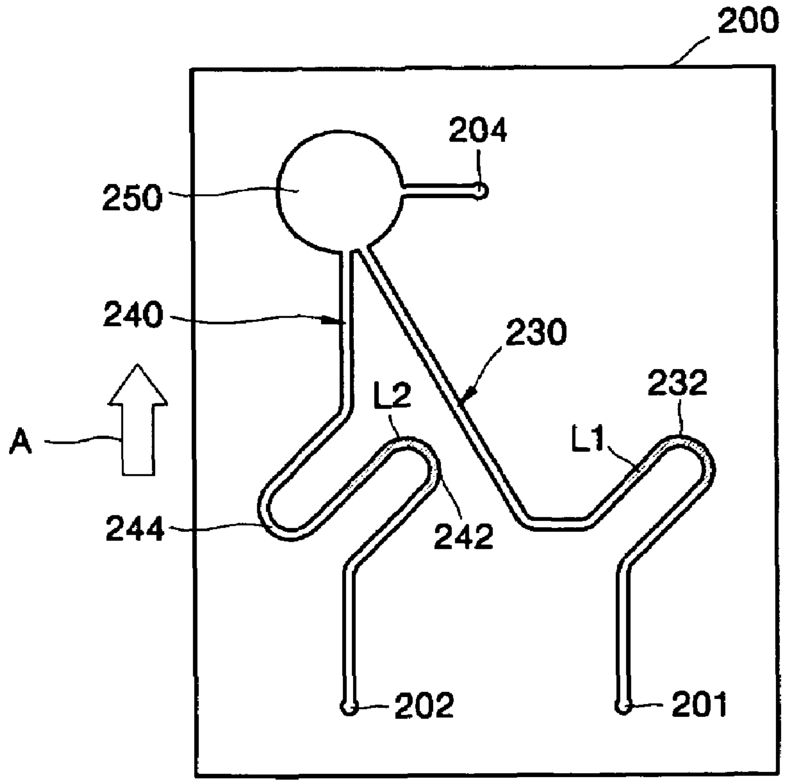

Referring to FIG. 4B, the first and second liquids L1 and L2 are trapped in the first traps 232 and 242, and do not move even the centrifugal force is continually applied to the microfluidic chip 200 in the first direction. The first traps 232 and 242 traps the first and second liquids L1 and L2 when the centrifugal force is applied in the first direction, or a second direction perpendicular to the first direction making an acute angle with respect to the first traps 232 and 242.

Figure 4C:
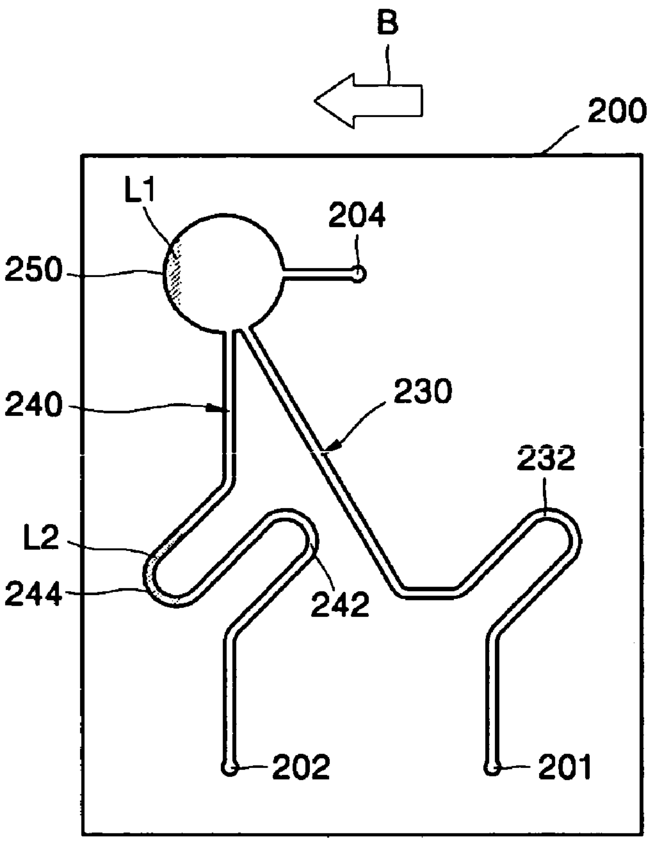

Referring to FIG. 4C, when the centrifugal force is applied to the microfluidic chip 200 in a third direction (an arrow B direction), the first liquid L1 flows to the chamber 250 from the first trap 232 and the second liquid L2 is trapped in the second trap 244. The second trap 242 traps the liquid L2 when the centrifugal force is applied to the microfluidic chip 200 in the third direction or a fourth direction opposite to the first direction.

Figure 4D:
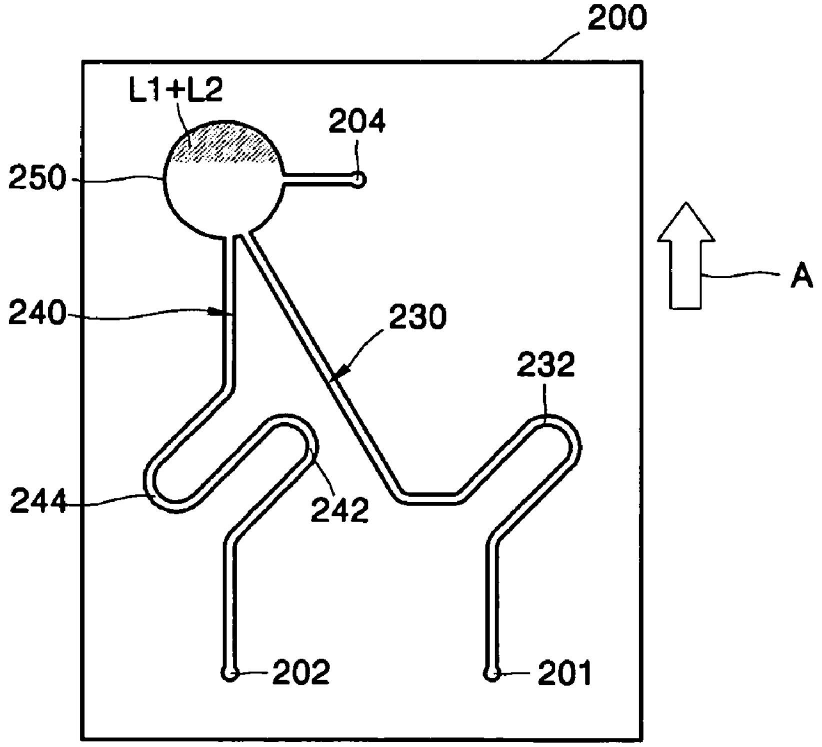

Referring to FIG. 4D, when a centrifugal force is applied to the microfluidic chip 200 in the first direction, the second liquid L2 trapped in the second trap 242 flows to the chamber 250. As a result, the first liquid L1 and the liquid 2 are mixed in the chamber 250.

Figure 4E:
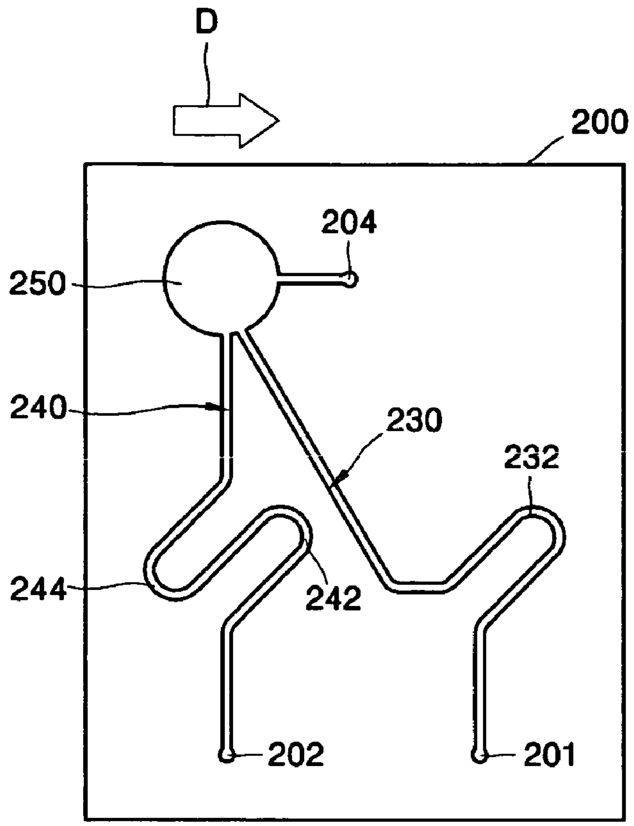

Referring to FIG. 4E, when a centrifugal force is applied to the microfluidic chip 200 in the second direction (an arrow D direction), the liquid mixture of the first liquid L1 and the second liquid L2 is exhausted through the outlet 104.

As described above, when different liquids L1 and L2 are injected into different microchannels 230 and 240 and the direction of a centrifugal force applied to the microfluidic chip 200 is changed, the time required for the liquids L1 and L2 to arrive at the chamber 250 can be independently controlled. In addition, many kinds of liquids can sequentially flow into the chamber 250 by forming three or more micro channels with different numbers of traps, though this is not illustrated in the drawings.

Once exhausted from the outlet 204, the mixture can react with another liquid by connecting the outlet 204 to another microchannel and changing the direction of an applied external force.

Figure 5:
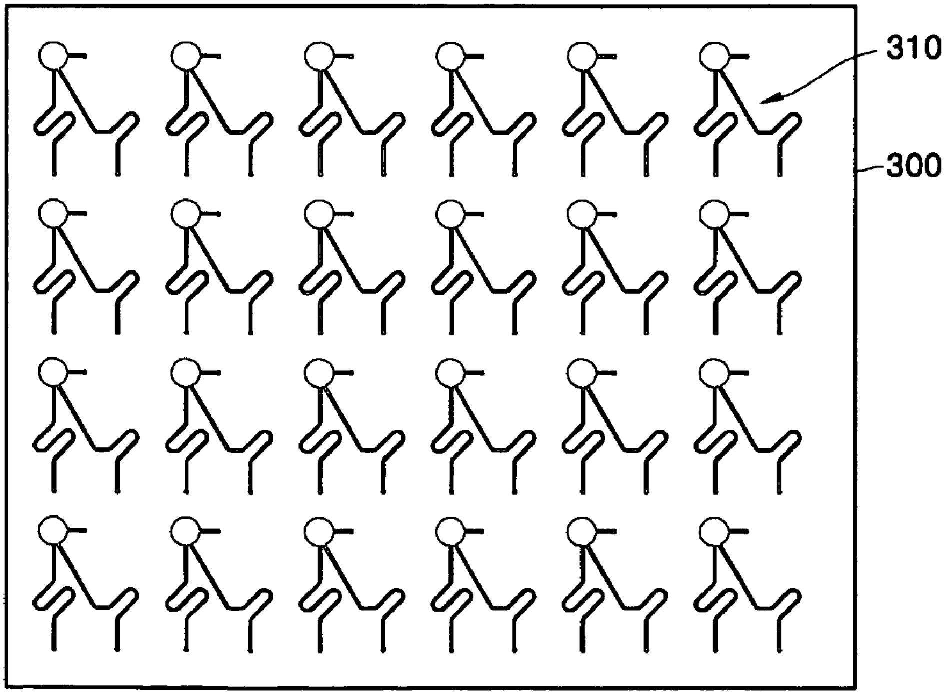
FIG. 5 is a plan view of a microfluidic chip according to a third embodiment of the present invention.

FIG. 5 is a plan view of a microfluidic chip 300 according to a third embodiment of the present invention.

Referring to FIG. 5, the microfluidic chip 300 includes a plurality of microfluidic manipulating units 310.

Liquids contained in the microfluidic manipulating units 310 of the microfluidic chip 300 according to the third embodiment of the present invention can be simultaneously moved and mixed when a force is applied to the microfluidic chip 300. Accordingly, pumps and valves required to manipulate the microfluidic manipulating units 310 can be formed of a microchannel and it is possible to simultaneously manipulate the microfluidic manipulating units 310.

Figure 6:
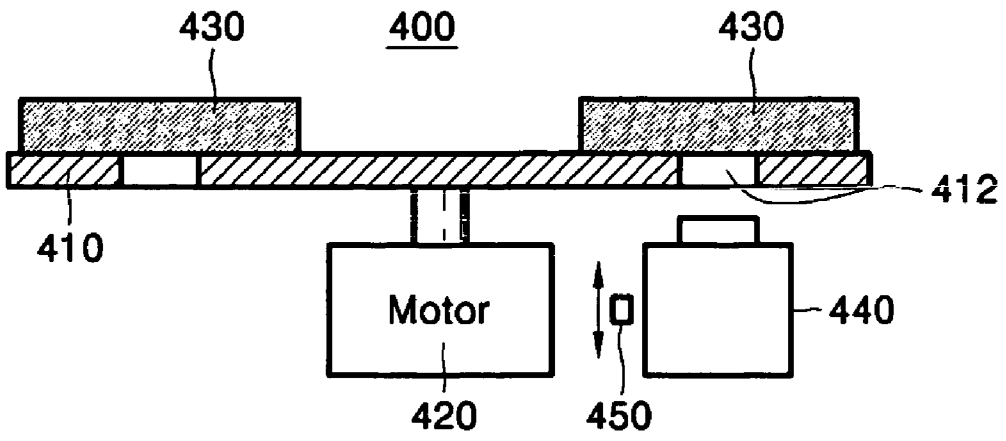
FIG. 6 is a sectional view of an apparatus for manipulating microfluid according to a fourth embodiment of the present invention.
Figure 7:
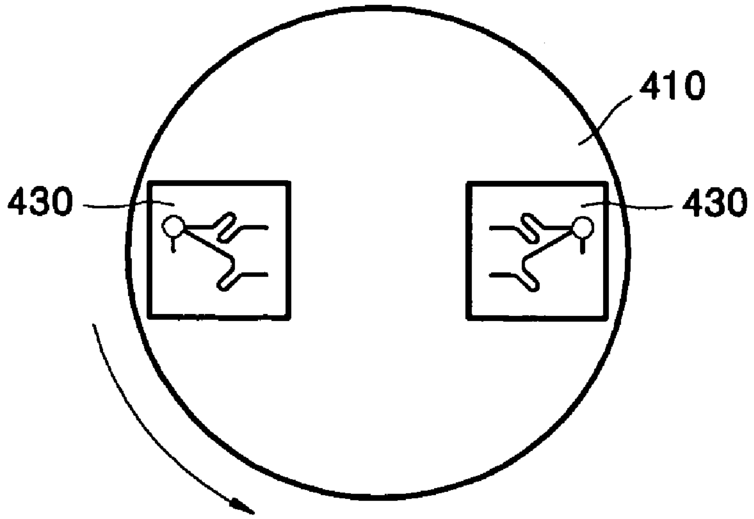
FIG. 7 is a plan view of the apparatus of manipulating microfluid illustrated in FIG. 6.

FIG. 6 is a sectional view of a microfluidic manipulating apparatus 400 according to a fourth embodiment of the present invention. FIG. 7 is a plan view of the microfluidic manipulating apparatus 400 illustrated FIG. 6.

Referring to FIGS. 6 and 7, the microfluidic manipulating apparatus 400 includes a disc 410 as a rotating plate, a first driving unit rotating the disc 410, and a second driving unit rotating a microfluidic chip 430 mounted on the disc 410. The first driving unit and the second driving unit may be a first motor 420 and a second motor 440, respectively.

The first motor 420 rotates the disc 410 in a direction at a predetermined rate such that a centrifugal force is applied to the microfluidic chip 430 disposed on the disc 410. A plurality of microfluidic chips 430 can be fixedly disposed on the disc 410. The second motor 440 is disposed under the disc 410. The second motor 440 can be connected to the microfluidic chip 430 through a hole 412 or separated from the lower portion of the disc 410 by an up-and-down transporting unit 450 below the disc 410. The second motor 440 rotates the microfluidic chip 430 such that the direction of a centrifugal force applied to the microfluidic chip 430 can be adjusted.

Figure 8A:
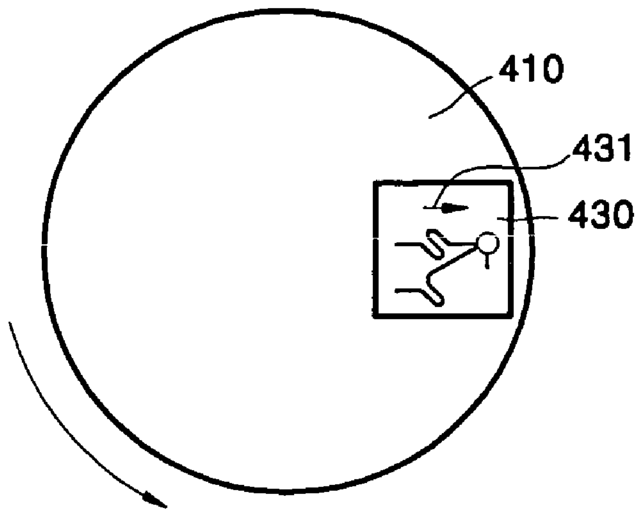
FIGS. 8A and 8B illustrate directions of centrifugal forces applied to microfluidic chips.
Figure 8B:
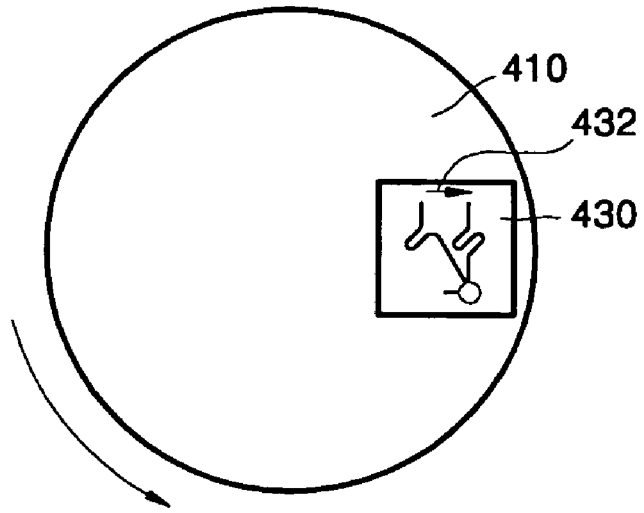

FIGS. 8A and 8B illustrate directions of centrifugal forces applied to the microfluidic chips 430.

Referring to FIG. 8A, when the disc 410 rotates in one direction, the microfluidic chip 430 is affected by a centrifugal force in a first direction 431.

Referring to FIG. 8B, the microfluidic chip 430 is rotated by an angle of 90° in a clockwise direction using a second motor 440, and the microfluidic chip 430 is affected by a centrifugal force in a second direction 432. Subsequently, the microfluidic chip 430 is further rotated by an angle of 90°, respectively, thus being affected by centrifugal forces in a third direction opposite to the first direction 431 and a fourth direction opposite to the second direction 432. Accordingly, when the first motor 420 rotates the disc 410, the microfluidic chip 430 is rotated by the second motor 440 and the direction of a centrifugal force applied to the microfluidic chip 430 can be adjusted. Thus, the movement of the microfluid contained in the microfluidic chip 430 can be manipulated.

Although, according to the fourth embodiment of the present invention, the disc 410 supports the microfluidic chip 430, the disc 410 can be replaced with a bar-shaped plate, for example.

In addition, the second motor 440 can be fixed to the disc 410, thus moving along with the disc 410 when the disc 410 is rotated by the first motor 420.

A microfluidic chip according to the present invention can easily trap or transfer liquid injected into the microfluidic chip using centrifugal force. That is, the liquid can be manipulated without the use of mechanical pumps and valves.

In addition, a single microfluidic chip may include a plurality of microfluidic manipulating units such that the microfluidic manipulating units can be simultaneously manipulated.

A microfluidic manipulating apparatus including a microfluidic trap according to the present invention can easily change the direction of a centrifugal force applied to microfluid.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A microfluidic chip comprising at least one microfluidic manipulating unit formed in a substrate, the microfluidic manipulating unit comprising:
- a plurality of microchannels formed in the substrate, each of the plurality of microchannels comprising:
  - an inlet formed at a first end of the microchannel and exposed through the substrate;
  - a first microchannel portion extending from the inlet in a first direction; and
  - a trap in fluid communication with the microchannel portion;
- a chamber connected to a second end of each of the plurality of microchannels; and
- an outlet connected to the chamber and exposed through the substrate;
- wherein the trap extends at an acute angle from the first microchannel portion.

2. The microfluidic chip of claim 1, wherein the trap is U-shaped.

3. The microfluidic chip of claim 2, wherein the trap comprises a first trap directly connected to the first microchannel portion. with respect to a first direction in which a liquid injected through the inlet flows.

4. The microfluidic chip of claim 3, wherein the trap further comprises a second trap formed between the first trap and the chamber.

5. The microfluidic chip of claim 4, wherein the second trap is formed in an opposite direction to a direction in which the first trap is formed.

6. The microfluidic chip of claim 4, wherein the outlet is formed substantially perpendicular to the first microchannel portion.

7. An apparatus for manipulating microfluid comprising:
- a rotating plate;
- a microfluidic chip fixedly disposed on the rotating plate;
- a first driving unit which rotates the rotating plate; and
- a second driving unit which rotates the microfluidic chip on the rotating plate,
- wherein the microfluidic chip comprises at least one microfluidic manipulating unit comprising:
- a plurality of microchannels formed in the substrate;
- an inlet formed at a first end of each of the plurality of microchannels and exposed through the substrate;
- a trap formed in each of the plurality of microchannels;
- a chamber connected to a second end of each of the plurality of microchannels; and
- an outlet connected to the chamber and exposed through the substrate.

8. The apparatus of claim 7, wherein the trap is U-shaped.

9. The apparatus of claim 7, wherein the trap makes an acute angel with respect to a first portion of an individual microchannel of the plurality of microchannels,the first portion of an individual microchannel extending from the inlet in a first direction.

10. The apparatus of claim 9, wherein the trap comprises a first trap,directly connected to the first portion of an individual microchannel.

11. The apparatus of claim 10, wherein the trap further comprises a second trap formed between the first trap and the chamber.

12. The apparatus of claim 11, wherein the second trap is formed in an opposite direction to a direction in which the first trap is formed.

13. The apparatus of claim 11, wherein the outlet is formed substantially perpendicular to the first portion of an individual microchannel of the plurality of microchannels.

14. The apparatus of claim 7, further comprising an up-and-down transporting unit that lifts the second driving unit with respect to the rotating plate such that the second driving unit is connected to or separated from the microfluidic chip.

15. The apparatus of claim 7, wherein the second driving unit is fixedly disposed on a lower surface of the rotating plate and moves along with the rotating plate.

16. A microfluidic chip comprising a microfluidic manipulating unit formed in a substrate, the microfluidic manipulating unit comprising:
- a microchannel formed in the substrate, the microchannel comprising:
  - an inlet formed at a first end of the microchannel and exposed through the substrate;
  - a first microchannel portion extending from the inlet in a first direction; and
  - a trap in fluid communication with the first microchannel portion;
- a chamber connected to a second end the microchannel; and
- an outlet connected to the chamber and exposed through the substrate,
- wherein the trap extends at an acute angle from the first microchannel portion.

* * * * *